(12) United States Patent
Bade et al.

(10) Patent No.: US 9,718,844 B2
(45) Date of Patent: Aug. 1, 2017

(54) PROCESS FOR PREPARING ALKENYLHALOSILANES AND REACTOR SUITABLE THEREFOR

(71) Applicants: Stefan Bade, Michelbach le Haut (FR); Norbert Schladerbeck, Kelkheim (DE)

(72) Inventors: Stefan Bade, Michelbach le Haut (FR); Norbert Schladerbeck, Kelkheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/416,952

(22) PCT Filed: May 28, 2013

(86) PCT No.: PCT/EP2013/060906
§ 371 (c)(1),
(2) Date: Jan. 23, 2015

(87) PCT Pub. No.: WO2014/016013
PCT Pub. Date: Jan. 30, 2014

(65) Prior Publication Data
US 2015/0274758 A1    Oct. 1, 2015

(30) Foreign Application Priority Data

Jul. 24, 2012    (DE) .................. 10 2012 212 913

(51) Int. Cl.
| | | |
|---|---|---|
| *B01J 19/00* | (2006.01) | |
| *C07F 7/14* | (2006.01) | |
| *B01J 19/24* | (2006.01) | |
| *B01J 4/00* | (2006.01) | |
| *C07F 7/12* | (2006.01) | |
| *B01J 19/26* | (2006.01) | |

(52) U.S. Cl.
CPC .............. *C07F 7/14* (2013.01); *B01J 4/002* (2013.01); *B01J 19/2415* (2013.01); *B01J 19/26* (2013.01); *C07F 7/122* (2013.01); *B01J 2219/0011* (2013.01); *B01J 2219/00051* (2013.01); *B01J 2219/00103* (2013.01); *B01J 2219/00123* (2013.01); *B01J 2219/00162* (2013.01); *B01J 2219/00166* (2013.01); *B01J 2219/24* (2013.01)

(58) Field of Classification Search
USPC ........................................ 422/630, 129, 234
See application file for complete search history.

(56) References Cited

U.S. PATENT DOCUMENTS

| | | | |
|---|---|---|---|
| 2,770,634 A | 11/1956 | Weyenberg | |
| 4,952,139 A | 8/1990 | Goldenberg | |
| 5,075,480 A | 12/1991 | Hange et al. | |
| 5,599,964 A * | 2/1997 | Roberg | B01J 19/1881 556/179 |
| 5,798,137 A | 8/1998 | Lord et al. | |
| 5,808,128 A | 9/1998 | Fiolitakis | |
| 6,222,056 B1 | 4/2001 | Bade et al. | |
| 8,722,141 B2 | 5/2014 | Weidhaus et al. | |

FOREIGN PATENT DOCUMENTS

| | | |
|---|---|---|
| DE | 936 445 | 12/1955 |
| DE | 197 27 576 | 5/1998 |
| DE | 199 18 115 | 10/2000 |
| DE | 10 2007 021 003 | 11/2008 |
| JP | 50-32110 | 3/1975 |
| JP | 60-97045 A | 5/1985 |
| JP | 64-38131 A | 2/1989 |
| JP | 2000-327687 A | 11/2000 |

(Continued)

OTHER PUBLICATIONS

U.S. Appl. No. 14/416,989, filed Jan. 23, 2015, Bade, et al.
German Search Result Issued Nov. 30, 2012 in German Application No. 10 2012 212 913.8 Filed Jul. 24, 2012.
Written Opinion of the International Searching Authority Issued Jul. 25, 2013 in PCT/EP13/060906 Filed May 28, 2013.
International Search Report Issued Jul. 25, 2013 in PCT/EP13/060906 Filed May 28, 2013.

*Primary Examiner* — Pancham Bakshi
(74) *Attorney, Agent, or Firm* — Oblon, McClelland, Maier & Neustadt, L.L.P.

(57) ABSTRACT

Described is a method for producing alkenyl halosilanes by reacting alkenyl halide selected from the group comprising vinyl halide, vinylidene halide, and allyl halide with halosilane selected from the group comprising monohalosilane, dihalosilane, and trihalosilane in the gas phase in a reactor comprising a reaction tube (1) that has an inlet (2) at one end and an outlet (3) at the other end, said reactor further comprising an annular-gap nozzle (4) that is mounted on the inlet (2), extends into the reaction tube (1), and has a central supply duct (5) for one reactant (7) and a supply duct (6), which surrounds the central supply duct (5), for the other reactant (8). In order to carry out said method, alkenyl halide is injected into the reaction tube (1) through the central supply duct (5), halosilane is injected thereinto through the surrounding supply duct (6), and both substances flow through the reaction tube (1) in the direction of the outlet (3). The described method allows alkenyl halosilanes to be produced at a high yield and with great selectivity. The amount of soot formed is significantly lower than in conventional reactors. The invention also relates to a reactor for carrying out gas-phase reactions, said reactor being characterized by at least the following elements: A) a reaction tube (1) that has B) an inlet (2) at one end, C) an outlet (3) at the other end, and D) an annular-gap nozzle (4) which includes a central supply duct (5) for one reactant (7) and a supply duct (6), which surrounds the central supply duct (5), for another reactant (8), said nozzle being mounted on the inlet (2) and extending into the reaction tube (1).

13 Claims, 1 Drawing Sheet

(56) References Cited

FOREIGN PATENT DOCUMENTS

| RU | 123959 | 11/1959 |
| SU | 1597091 | 9/1990 |
| WO | WO 2014/016014 A1 | 1/2014 |

* cited by examiner

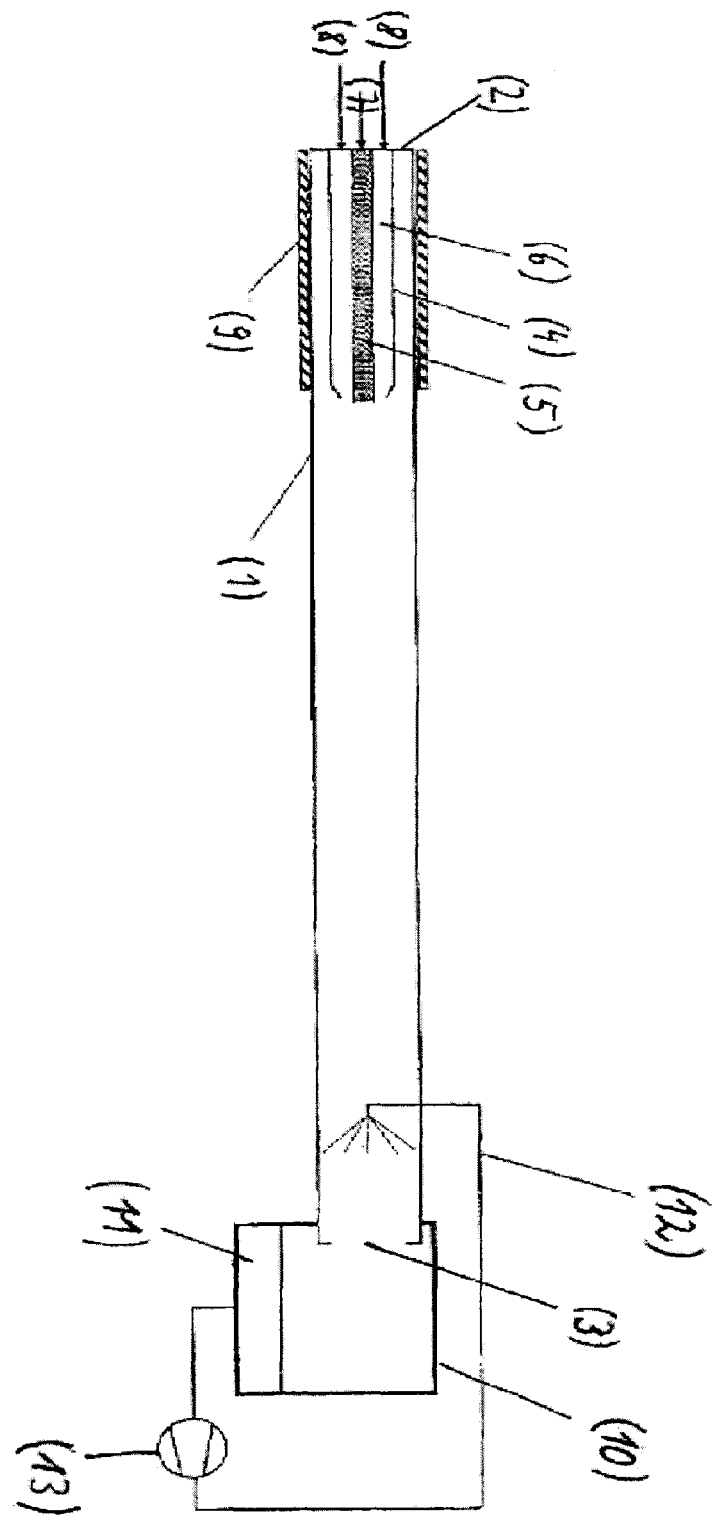

PROCESS FOR PREPARING ALKENYLHALOSILANES AND REACTOR SUITABLE THEREFOR

The present invention relates to a process for preparing alkenylhalosilanes, especially vinyltrichlorosilane, from vinyl chloride and trichlorosilane, and to a reactor particularly suitable therefor.

The industrial scale preparation of alkenylhalosilanes is common knowledge. As a representative example of the preparation of alkenylhalosilanes, the industrial scale preparation of vinyltrichlorosilane (III) is described here in detail. This is effected from the raw materials vinyl chloride (I) and trichlorosilane (II). In a free-radical high-temperature reaction, silane (II) is combined with vinyl chloride (I), with elimination of hydrogen chloride (IV), according to the following reaction scheme (1):

$$C_2H_3Cl\ (I) + SiHCl_3\ (II) \rightarrow C_2H_3SiCl_3\ (III) + HCl\ (IV) \qquad (1)$$

Alkenylhalosilanes, such as vinyltrichlorosilane (III), especially the group of the vinyltrialkoxysilanes prepared from the compound (III) via esterification reactions, are important industrial intermediates and end products in organosilane chemistry. They find use, for example, as crosslinkers in plastics such as PVC, PP and PE.

As well as the main reaction shown above, several unwanted side reactions proceed in the course of conversion. Examples of these include:

A) formation of silicon tetrachloride (V) according to scheme (2) below:

$$SiHCl_3\ (II) + HCl\ (IV) \rightarrow SiCl_4\ (V) + H_2\ (VI) \qquad (2)$$

B) formation of bis(trichlorosilyl)ethane (VII) according to scheme (3) below:

$$SiHCl_3\ (II) + C_2H_3SiCl_3\ (III) \rightarrow Cl_3Si\ C_2H_4SiCl_3\ (VII) \qquad (3)$$

C) formation of soot (VIII) according to the following scheme (4):

$$C_2H_3Cl\ (I) \rightarrow 2C\ (VIII) + HCl\ (IV) + H_2\ (VI) \qquad (4)$$

The free-radical exothermic substitution reaction between vinyl chloride and trichlorosilane proceeds typically in a high-temperature reactor within the temperature range between 400 and 700° C. and a pressure between 1 and 2 bar abs. The standard processes are characterized in that either a tubular reactor or a reactor having a rotating displacement body is used. Examples thereof can be found in EP 0 438 666 A2, DE 199 18 114 A1 and DE 199 18 115 A1.

The existing processes have several disadvantages. These are the by-products that form as a result of backmixing, wall reactions that lead, for example, to the formation of soot (reaction scheme 4), and the difficulty of temperature control.

In addition, the conversion of the vinyl chloride can be set only in the range of 80% at maximum, in which case the selectivity based on vinyltrichlorosilane is about 86% at maximum. At conversions of >80%, the selectivity falls considerably because of the side reactions that proceed.

As a result of soot formation in the use of conventional reactors, they have to be shut down and cleaned at regular intervals.

EP 0 438 666 A2 describes an annular gap reactor having a gap measurement of 20 mm. The annular gap is formed by means of a rotating displacement body within the reactor shell. Documents DE 199 18 114 A1 and DE 199 18 115 A1 likewise describe an annular gap reactor for the production of vinyltrichlorosilane, in which the stream, after flowing through the annular gap, runs through an adiabatic reaction zone and then the reaction gases are quenched.

A typical process regime known from DE 199 18 115 A1 results in a vinyl chloride conversion of 85% and a vinyltrichlorosilane selectivity, based on vinyl chloride converted, of 88%. Feeding in 100 kg/h of vinyl chloride and 700 kg/h of trichlorosilane results in the following mass flow rates in the reaction mixture at the reactor outlet:

| | |
|---|---|
| vinyl chloride = 14.9 kg/h | trichlorosilane = 495.2 kg/h |
| vinyltrichlorosilane = 193.3 kg/h | hydrogen chloride = 43.6 kg/h |
| silicon tetrachloride = 38.1 kg/h | high boilers/further secondary components = 15.1 kg/h |

The production output of the reactor described is 139 t of vinyltrichlorosilane per month or, in specific terms, 900 kg/(m$^3$*th) as the space-time yield.

A typical process regime known from DE 199 18 114 A1 results in a vinyl chloride conversion of 86% and a vinyltrichlorosilane selectivity, based on VC converted, of 89%. Feeding in 70 kg/h of vinyl chloride and 420 kg/h of trichlorosilane results in the following mass flow rates in the reaction mixture at the reactor outlet:

| | |
|---|---|
| vinyl chloride = 9.8 kg/h | trichlorosilane = 274.8 kg/h |
| vinyltrichlorosilane = 138.5 kg/h | hydrogen chloride = 32.2 kg/h |
| silicon tetrachloride = 20.8 kg/h | high boilers/further secondary components = 15.5 kg/h |

The production output of the annular gap reactor described is 100 t of vinyltrichlorosilane per month or, in specific terms, 648 kg/(m$^3$*h) as the space-time yield.

These two comparative examples describe maximum vinyl chloride conversions of 86%, maximum vinyltrichlorosilane selectivities of 89% and a maximum vinyltrichlorosilane space-time yield of 900 kg/(m$^3$*h).

It has now been found that, surprisingly, use of a novel reactor of the "nozzle reactor" type allows the yield and selectivity based on the alkenylhalosilane target product, especially of vinyltrichlorosilane (III), to be distinctly increased compared to the existing processes. Furthermore, the process regime is gentle, such that the tendency for side reactions to proceed can be distinctly reduced, and the formation of by-products, such as soot, can be drastically reduced.

The problem addressed by the present invention is that of providing a process and a reactor suitable therefor for preparation of alkenylhalosilanes having increased yield and selectivity compared to known processes and reactors, and having a reduced tendency to side reactions.

The present invention relates to a process for preparing alkenylhalosilanes by reacting alkenyl halide selected from the group of vinyl halide, vinylidene halide and allyl halide with halosilane selected from the group of mono-, di- and trihalosilane in the gas phase in a reactor comprising a reaction tube (1) equipped with an inlet (2) at one end of the tube and with an outlet (3) at the other end of the tube, and having an annular gap nozzle (4) which has a central feed (5) for one reactant (7) and a feed (6) surrounding the central feed (5) for the other reactant (8) and is mounted at the inlet (2) and opens into the reaction tube (1), wherein alkenyl halide is injected into the reaction tube (1) through the central feed (5) and halosilane through the surrounding feed (6), and they flow through the reaction tube (1) in the direction of outlet (3).

In the context of this description, halogen is understood to mean fluorine, chlorine, bromine or iodine, preferably chlorine and bromine, especially chlorine.

The vinyl halides used in accordance with the invention are vinyl fluoride, vinyl chloride, vinyl bromide and vinyl iodide, or mixtures of two or more thereof. Preference is given to using vinyl chloride and/or vinyl bromide, most preferably vinyl chloride.

The vinylidene halides used in accordance with the invention are vinylidene fluoride, vinylidene chloride, vinylidene bromide and vinylidene iodide, or mixtures of two or more thereof. Preference is given to using vinylidene chloride and/or vinylidene bromide, most preferably vinylidene chloride.

The allyl halides used in accordance with the invention are allyl fluoride, allyl chloride, allyl bromide and allyl iodide, or mixtures of two or more thereof. Preference is given to using allyl chloride and/or allyl bromide, most preferably allyl chloride.

The monohalosilanes used in accordance with the invention are monofluorosilane, monochlorosilane, monobromosilane and monoiodosilane, or mixtures of two or more thereof. Preference is given to using monochlorosilane and/or monobromosilane, most preferably monochlorosilane.

The dihalosilanes used in accordance with the invention are compounds of the formula (Hal1)(Hal2)SiH$_2$ where Hal1 and Hal2 are each independently fluorine, chlorine, bromine or iodine. Examples of dihalosilanes are difluorosilane, dichlorosilane, dibromosilane, diiodosilane or mixed types, such as chlorobromosilane, fluorochlorosilane or chloroiodosilane. Mixtures of two or more thereof may also be involved. Preference is given to using dihalosilanes in which Hal1 and Hal2 are the same. Very particular preference is given to using dichlorosilane and/or dibromosilane, and especially dichlorosilane.

The trihalosilanes used in accordance with the invention are compounds of the formula (Hal1)(Hal2)(Hal3)SiH where Hal1, Hal2 and Hal3 are each independently fluorine, chlorine, bromine or iodine. Examples of trihalosilanes are trifluorosilane, trichlorosilane, tribromosilane, triiodosilane or mixed types, such as fluorochlorobromosilane, dichlorobromosilane or chlorodibromosilane. Mixtures of two or more thereof may also be involved. Preference is given to using trihalosilanes in which Hal1, Hal2 and Hal3 are the same. Very particular preference is given to using trichlorosilane and/or tribromosilane, and especially trichlorosilane.

Very particular preference is given to reacting trichlorosilane and vinyl chloride or trichlorosilane and allyl chloride with one another.

In the inventive reactor, the alkenyl halide is injected centrally, i.e. at the site of the longitudinal axis of the reaction tube (1), together with the halosilane. In this case, the latter is injected into the reaction tube (1) as a gas stream flanking the stream of the alkenyl halide. The reactor has low backmixing and the reactions are kept away from the reactor wall, which leads to reduced formation of by-products.

In addition, the reaction regime (=sheathing of the alkenyl halide stream by the halosilane stream) produces an optimal temperature profile in the reactor, as a result of which the selectivity and space-time yield based on the alkenylhalosilane target product can be increased in a particularly advantageous manner.

The avoidance of rotating internals, as described in EP 0 438 666 A2, DE 199 18 114 A1 and DE 199 18 115 A1, makes the construction of the reactor much simpler and less demanding in terms of maintenance.

In the process according to the invention, the mono-, di- or trihalosilane is injected into the reaction tube (1) completely through the central feed (5) of the annular gap nozzle (4), close to the inlet (2).

The surrounding feed (6) of the annular gap nozzle provides a gas feed point for the alkenyl halide into the reaction tube (1).

By varying the flow rate of the reactants (7, 8) in the annular gap nozzle (4), the course of the reaction can be controlled. Preferably, therefore, means by which the flow rate of the alkenyl halide and/or of the halosilane can be varied are provided in the annular gap nozzle (4).

The reaction can likewise be controlled via the use ratio of mono-, di- or trihalosilane to alkenyl halide. Typically, the use ratio of mono-, di- or trihalosilane to alkenyl halide is between 1.0 and 10 mol:mol, preferably between 2.0 and 4.0 mol:mol.

At the end of the reaction tube (1), the reaction of mono-, di- or trihalosilane with alkenyl halide has substantially concluded. The product-containing reaction mixture can be discharged from the reaction tube (1) via the outlet (3) and sent to further operations, for example a separation of the alkenylhalosilane product from the reaction mixture.

Preferably, the hot reaction mixture is quenched at the product end of the reaction tube (1). This can preferably be effected with liquid crude product, which is preferably injected into the hot reaction mixture at the product end of the reaction tube (1).

In the process according to the invention, the reaction temperature can be chosen within wide ranges. Preferably, the temperature in the interior of the reaction tube (1) (=the reaction temperature) is between 400 and 700° C., more preferably between 500 and 650° C.

In the process according to the invention, the reaction pressure can likewise be chosen within wide ranges. Preferably, the pressure in the interior of the reaction tube (1) (=reaction pressure) is between 1.0 and 2.0 bar abs, more preferably between 1.0 and 1.5 bar abs.

The course of the reaction can be controlled by the amount of the reactants added. Preferably, the flow rate of the alkenyl halide in the central feed (5) is set in a controlled manner. The control can be effected by means of a closed-loop temperature control circuit in the annular gap nozzle (4).

The residence time of the reaction mixture in the reactor can likewise be varied over wide ranges. Typically, the residence time of the reaction mixture in the reactor from the opening of the annular gap nozzle (4) to the outlet (3) varies within the range between 0.5 and 10 sec, preferably between 1.5 and 4 sec.

The present invention also relates to a tubular reactor suitable for performance of gas phase reactions and especially for performance of the above-described process preparing alkenylhalosilane.

The inventive reactor is characterized by the presence of at least the following elements:
A) reaction tube (1) having
B) an inlet (2) at one side of the tube,
C) an outlet (3) at the other side of the tube, and
D) having an annular gap nozzle (4) having a central feed (5) for one reactant (7) and a feed (6) surrounding the central feed (5) for the other reactant (8), which is mounted at the inlet (2) and opens into the reaction tube (1).

The materials from which both the reaction tube (1) thus also the annular gap nozzle (4) are produced are stable to high temperatures. These materials include, for example, ferrous alloys, for example scale-resistant steels containing, as well as iron, chromium, nickel and/or titanium and/or molybdenum as alloy constituent.

The reactor for preparation of alkenylhalosilanes by reaction of alkenyl halide with mono-, di- or trihalosilanes may be arranged horizontally, vertically, or else obliquely. The way in which the reactor has been mounted has no influence on the alkenylhalosilane yields of the reaction unit. It has been found, however, that the service life of the reactors arranged vertically is much longer than that of reactors which are operated in a horizontal position.

The reactor, i.e. the outer reaction tube (1), can be heated in a wide variety of different ways. The most frequently used method involves the direct electrical heating of the outer surface of the reaction tube (1). Another form of heating involves heating the outer tube by means of an intervening medium, for example liquid lead. It is also possible to heat the outer tube by means of gas flames or by means of infrared radiation. The way in which the reactor is heated has only an insignificant effect on the conversions achievable per unit of cross-sectional area of the reactor.

Preference is given to a reactor in which, in a preheating zone (6) connected to the inlet (2), the reactants (7, 8) are heated to the required reaction temperature in the interior of the reaction tube (1).

Preference is likewise given to a reactor in which means provided at the central feed (5) and/or at the surrounding feed (6) can be used to vary the flow rate of the reactant(s) in the annular gap nozzle (4).

In a further preferred reactor, in a preheating zone (6) connected to the inlet (2), the reactants (7, 8) are heated to the required reaction temperature.

In a further preferred reactor, the outlet (3) opens into a reservoir vessel (10) for the cooled product (11). In this variant, a line (12) through which a portion of the product (11) is recycled close to the outlet (3) and is injected into the reaction mixture present at that point is preferably provided, and this brings about shock cooling of the reaction mixture and formation of the cooled product (11).

FIG. 1 describes the process according to the invention and the reactor according to the invention. This shows the reaction tube (1) equipped on the left-hand side with an inlet (2) for the reactants (7, 8), for example for vinyl chloride and for trichlorosilane. In a preheating zone (9) connected to the inlet (2), the reactants (7, 8) are heated to the required reaction temperature. An annular gap nozzle (4) having a central feed (5) for alkenyl halide (7) and a feed (6) surrounding the latter for halosilane opens into the reaction tube (1). The annular gap nozzle (4) opens into the reaction tube (1) such that the alkenyl halide and a mist of halosilane surrounding the latter can be injected into the reaction tube. The reaction tube (1) ends on the right-hand side with an outlet (3) for the reaction mixture. This outlet (3) opens into a reservoir vessel (10) for the cooled product (11). A portion of the product (11) is recycled via a line (12), under the action of the pump (13), close to the outlet (3) and is injected into the reaction mixture present at that point. This results in shock cooling of the reaction mixture and formation of the cooled product (9). This is then passed via outlet (3) into the reservoir vessel (10).

The example below describes the invention in specific detail, without any intention of limitation thereby.

Vinyl chloride was reacted with trichlorosilane in a nozzle reactor (diameter 200 mm, length 6000 mm) to give vinyltrichlorosilane. The trichlorosilane and vinyl chloride reactants were preheated here to 400° C. in a preheating zone. At the top of the reactor was a two-phase nozzle in which the two reactants were fed in separately. Vinyl chloride was injected in the middle of the axis, while trichlorosilane was fed in in an annular gap around the vinyl chloride feed. On exit of the vinyl chloride from the nozzle, the reaction to give vinyltrichlorosilane then ensued in the ensheathing trichlorosilane stream. The reaction zone was kept away from the reactor wall here by the ensheathing trichlorosilane fed in in excess. The result was a pure gas phase reaction between trichlorosilane and vinyl chloride. The yield-reducing wall reactions which lead to the formation of soot, for example, were prevented.

The reaction proceeds continuously in the tubular reactor connected to the annular gap nozzle (4). At the end of the reactor, there was a quench of the hot reaction gas with liquid crude product, which very substantially suppressed further reaction to give silicon tetrachloride.

In the example, 100 kg/h of gaseous vinyl chloride (centre of tube) and 650 kg/h of trichlorosilane (via an annular gap around the vinyl chloride feed) were fed in at 450° C. at the reactor inlet. In the first part of the reactor, the reactant mixture stream was heated further to about 500° C. Then the reaction began to proceed noticeably, and a reaction zone formed, which had its highest temperatures at about 625° C. At the position in the reactor where the gas stream reached the temperature of 630° C., the hot reaction gas was quenched with liquid crude product to about 40° C. The vinyl chloride conversion was 83%; the selectivity was 92%.

The reactor used had a diameter of 200 mm and a length of 6000 mm. The following mass flow rates of the reaction mixture at the reactor outlet were found:

| | |
|---|---|
| vinyl chloride = 17.0 kg/h | trichlorosilane = 457.1 kg/h |
| vinyltrichlorosilane = 197.3 kg/h | hydrogen chloride = 44.5 kg/h |
| silicon tetrachloride = 20.6 kg/h | high boilers/further secondary components = 13.5 kg/h |

Thus, this reactor had a monthly production output of 142 t of vinyltrichlorosilane and a space-time yield of 1046 kg/(m$^3$*h). A higher space-time yield was achieved than in the above-described comparative examples with prior art reactors, and the vinyltrichlorosilane selectivity of the nozzle reactor used, at 92%, was likewise higher than in the comparative examples. The higher vinyltrichlorosilane selectivity was achieved by virtue of a lower incidence of silicon tetrachloride by-product and of high boilers or further secondary components.

The construction of the nozzle was such that the vinyl chloride was introduced in the centre of the tube via an exit orifice of 25 mm. Around the vinyl chloride feed was an annular gap with s=2 mm and Da=35 mm for the trichlorosilane feed.

Advantages of the process according to the invention and of the reactor of the "nozzle reactor" type according to the invention are found to be the enhanced selectivity and the enhanced space-time yield based on the vinyltrichlorosilane target product, because wall reactions are selectively prevented through the ensheathing with a trichlorosilane stream. Moreover, the reactor can be described as having low backmixing, as a result of which a lower level of by-products, for example silicon tetrachloride, soot and 1,2-bis(trichlorosilyl)ethane, is formed in the reaction system in question.

By virtue of the wall reaction being very substantially prevented through the flanking with trichlorosilane, the formation of soot is minimized and the intervals for the cleaning operations of the reactor are extended.

The nozzle reactor used in accordance with the invention can be operated with a distinctly increased vinyl chloride conversion, because it works with low backmixing. This increases the space-time yield of vinyltrichlorosilane compared to the reactants used conventionally.

The invention claimed is:

1. A reactor suitable for gas phase reactions, comprising: a reaction tube comprising
an inlet at one side of the tube,
   an outlet at the other side of the tube, the outlet opening to a reservoir vessel suitable to contain a cooled product of the gas phase reaction,
   an annular gap nozzle comprising a central feed for one reactant and a feed surrounding the central feed for another reactant, which is mounted at the inlet and opens into the reaction tube, wherein the feed surrounding the central feed has a side wall angled towards the central feed of the annular gap nozzle
   a preheating zone connected to the inlet in such a way so as to heat reactants for the gas phase reaction to a reaction temperature, and
a line connected from the reservoir to near the outlet, the line configured to recycle the cooled product in the reaction mixture.

2. The reactor according to claim 1, further comprising a means to vary the flow rate of the reactant(s) in the annular gap nozzle positioned at the central feed and/or at the feed surrounding the central feed.

3. A process for preparing alkenylhalosilanes by reacting alkenyl halide selected from the group consisting of vinyl halide, vinylidene halide and allyl halide with halosilane selected from the group consisting of mono-, di- and trihalosilane in the gas phase in the reactor according to claim 1 wherein the alkenyl halide is injected into the reaction tube through the central feed and halosilane through the surrounding feed, and they flow through the reaction tube in the direction of outlet (3).

4. The process according to claim 1, wherein the alkenyl halide is vinyl chloride, vinyl bromide, vinylidene chloride, vinylidene bromide, allyl chloride or allyl bromide, and the halosilane is di- or trichlorosilane or di- or tribromosilane.

5. The process according to claim 1, wherein the alkenyl halide is vinyl chloride or allyl chloride, and the halosilane is trichlorosilane.

6. The process according to claim 1, characterized in that the annular gap nozzle is a two-phase nozzle.

7. The process according to claim 1, wherein the reactor further comprises a device to vary the flow rate of the reactant(s) positioned at the central feed and/or at the feed surrounding the central feed.

8. The process according to claim 1, wherein the mono-, di- or trihalosilane to alkenyl halide is in a ratio of 1.0 to 10 mol:mol.

9. The process according to claim 1, wherein a hot reaction mixture is quenched with a liquid crude product at the product end of the reaction tube.

10. The process according to claim 1, wherein the temperature in the interior of the reaction tube is between 400 and 700° C.

11. The process according to claim 1, wherein the pressure in the interior of the reaction tube is from 1.0 to 2.0 bar abs.

12. The process according to claim 1, wherein the flow rate of the alkenyl halide in central feed is controlled by a closed-loop temperature control circuit.

13. The process according to claim 1, wherein the residence time of the reaction mixture in the reactor from opening of the annular nozzle to the outlet is 0.5 to 10 sec.

* * * * *